United States Patent
Myllyoja et al.

(10) Patent No.: US 10,364,396 B2
(45) Date of Patent: *Jul. 30, 2019

(54) METHOD FOR THERMAL CONVERSION OF KETOACIDS AND HYDROTREAMENT TO HYDROCARBONS

(71) Applicant: NESTE OYJ, Espoo (FI)

(72) Inventors: Jukka Myllyoja, Vantaa (FI); Rami Piilola, Helsinki (FI)

(73) Assignee: NESTE OYJ, Espoo (FI)

(*) Notice: Subject to any disclaimer, the term of this patent is extended or adjusted under 35 U.S.C. 154(b) by 0 days.

This patent is subject to a terminal disclaimer.

(21) Appl. No.: 15/276,144

(22) Filed: Sep. 26, 2016

(65) Prior Publication Data
US 2017/0073588 A1  Mar. 16, 2017

Related U.S. Application Data

(63) Continuation of application No. PCT/FI2015/050209, filed on Mar. 26, 2015.

(30) Foreign Application Priority Data

Mar. 26, 2014 (EP) ..................... 14161792

(51) Int. Cl.
*C07C 1/20* (2006.01)
*C10G 3/00* (2006.01)
(Continued)

(52) U.S. Cl.
CPC .............. *C10G 3/50* (2013.01); *C07C 49/04* (2013.01); *C07C 51/353* (2013.01); *C07C 57/13* (2013.01);
(Continued)

(58) Field of Classification Search
CPC ......... C07C 57/13; C07C 55/02; C07C 59/19; C07C 59/195; C10G 3/50; C10G 3/40
(Continued)

(56) References Cited

U.S. PATENT DOCUMENTS 2,440,751 A  5/1948 Legatski
5,254,794 A  10/1993 Wu
(Continued)

FOREIGN PATENT DOCUMENTS

CN  102449118 A  5/2012
CN  102676201 A  9/2012
(Continued)

OTHER PUBLICATIONS

Bankole, K.S. "Uncatalyzed esterification of biomass-derived carboxylic acids", (2011), pp. 1-136.*
(Continued)

*Primary Examiner* — Philip Y Louie
*Assistant Examiner* — Aaron W Pierpont
(74) *Attorney, Agent, or Firm* — Buchanan Ingersoll & Rooney PC (57) ABSTRACT

The present disclosure relates to thermal conversion of ketoacids, including methods for increasing the molecular weight of ketoacids, the method including the steps of providing in a reactor a feedstock comprising at least one ketoacid. The feedstock is then subjected to one or more C-C-coupling reaction(s) by heating the feedstock to temperature of 200-500° C. in the absence of a catalyst.

12 Claims, 8 Drawing Sheets

Process scheme for upgrading C-C coupling reactions (51) Int. Cl.
*C10G 50/00* (2006.01)
*C10L 1/02* (2006.01)
*C07C 49/04* (2006.01)
*C07C 51/353* (2006.01)
*C07C 57/13* (2006.01)

(52) U.S. Cl.
CPC ............... *C10G 3/40* (2013.01); *C10G 3/42* (2013.01); *C10G 3/46* (2013.01); *C10G 3/48* (2013.01); *C10G 50/00* (2013.01); *C10L 1/023* (2013.01); *C10L 1/026* (2013.01); *C10G 2300/1014* (2013.01); *C10G 2400/02* (2013.01); *C10G 2400/04* (2013.01); *C10L 2200/0469* (2013.01); *C10L 2270/023* (2013.01); *Y02P 30/20* (2015.11)

(58) Field of Classification Search
USPC .......................................................... 585/14
See application file for complete search history.

(56) References Cited

U.S. PATENT DOCUMENTS

| | | | |
|---|---|---|---|
| 5,345,026 | A | 9/1994 | Chang et al. |
| 5,382,731 | A | 1/1995 | Chang et al. |
| 5,608,105 | A | 3/1997 | Fitzpatrick |
| 6,206,940 | B1 | 3/2001 | Weissman et al. |
| 8,003,818 | B2 | 8/2011 | Van Den Brink et al. |
| 8,362,306 | B2 | 1/2013 | Wheeler et al. |
| 8,629,310 | B2 | 1/2014 | Lotero et al. |
| 9,120,712 | B2 | 9/2015 | Wheeler et al. |
| 2006/0135793 | A1 | 6/2006 | Blessing et al. |
| 2006/0162239 | A1 | 7/2006 | Van Den Brink et al. |
| 2009/0014354 | A1* | 1/2009 | Knuuttila ............... C10G 29/22 208/58 |
| 2010/0312028 | A1 | 12/2010 | Olson et al. |
| 2011/0098503 | A1* | 4/2011 | Wheeler ................. C07C 5/333 562/594 |
| 2012/0203043 | A1* | 8/2012 | Wheeler ............... C07C 1/2078 585/242 |
| 2012/0209037 | A1 | 8/2012 | Viljoen et al. |
| 2012/0283493 | A1 | 11/2012 | Olson et al. |
| 2013/0237728 | A1 | 9/2013 | Lotero et al. |
| 2015/0018581 | A1 | 1/2015 | Kettunen et al. |
| 2015/0018588 | A1 | 1/2015 | Myllyoja et al. |

FOREIGN PATENT DOCUMENTS

| | | |
|---|---|---|
| CN | 103391987 A | 11/2013 |
| GB | 601922 A | 5/1948 |
| GB | 762136 A | 11/1956 |
| WO | WO 95/03262 A1 | 2/1995 |
| WO | WO 00/47697 A1 | 8/2000 |
| WO | WO 2006/056591 A1 | 6/2006 |
| WO | WO 2006/067171 A1 | 6/2006 |
| WO | WO 2011/053584 A1 | 5/2011 |
| WO | WO 2013/113976 A1 | 8/2013 |

OTHER PUBLICATIONS

Farrauto, et. al. "Introduction to Catalysis and Industrial Catalytic Processes", John Wiley & Sons, Inc.: Hoboken, New Jersey (2016); pp. 1 and 2. (Year: 2016).*
International Search Report (PCT/ISA/210) dated Jul. 3, 2015, by the Finnish Patent Office as the International Searching Authority for International Application No. PCT/FI2015/050208.
International Search Report (PCT/ISA/210) dated Aug. 13, 2015, by the Finnish Patent Office as the International Searching Authority for International Application No. PCT/FI2015/050209.
International Search Report (PCT/ISA/210) dated Aug. 24, 2015, by the European Patent Office as the International Searching Authority for International Application No. PCT/EP2015/056655.
Office Action (The First Office Action) dated Dec. 25, 2017, by the State Intellectual Property Office (SIPO) of the People's Republic of China in corresponding Chinese Patent Application No. 201580016135.X and an English Translation of the Office Action. (15 pages).

* cited by examiner

Figure 1 – Conversion of lignocellulosic material to levulinic acid

Figure 2 – Process scheme for upgrading C-C coupling reactions

Figure 3 – Process scheme

Figure 4 – Chromatogram from Example 1

Figure 5 – Chromatogram from Example 5, distillate

Figure 6 – Chromatogram from Example 5, bottom

Figure 7 – Chromatogram from Example 6, distillate

Figure 8 – Chromatogram from Example 6, bottom

METHOD FOR THERMAL CONVERSION OF KETOACIDS AND HYDROTREAMENT TO HYDROCARBONS

CROSS-REFERENCE TO RELATED APPLICATIONS

This application claims priority as a continuation application under 35 U.S.C. § 120 to PCT/FI2015/050209, which was filed as an International Application on Mar. 26, 2015 designating the U.S., and which claims priority to European Application 14161792.8 filed in Europe on Mar. 26, 2014. The entire contents of these applications are hereby incorporated by reference in their entireties.

FIELD

The present disclosure relates to thermal conversion of ketoacids in the absence of a catalyst, including methods for increasing the molecular weight of ketoacids, C C coupling reaction products obtainable by such methods, as well as use of such products for the production of liquid hydrocarbons and/or diesel fuel components. The present disclosure also relates to hydrocarbon compositions, for example, gasoline fractions.

BACKGROUND INFORMATION

Production of hydrocarbons used as fuel or heavy oil components and chemicals from biomass are of increasing interests since they are produced from a sustainable source of organic compounds.

Figure 1:
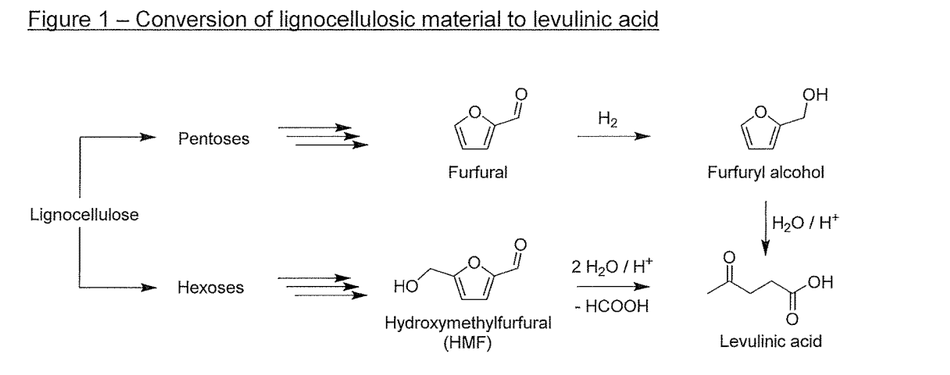
FIG. 1 shows a scheme illustrating conversion of lignocellulosic material to levulinic acid, according to an exemplary aspect.
Figure 2:
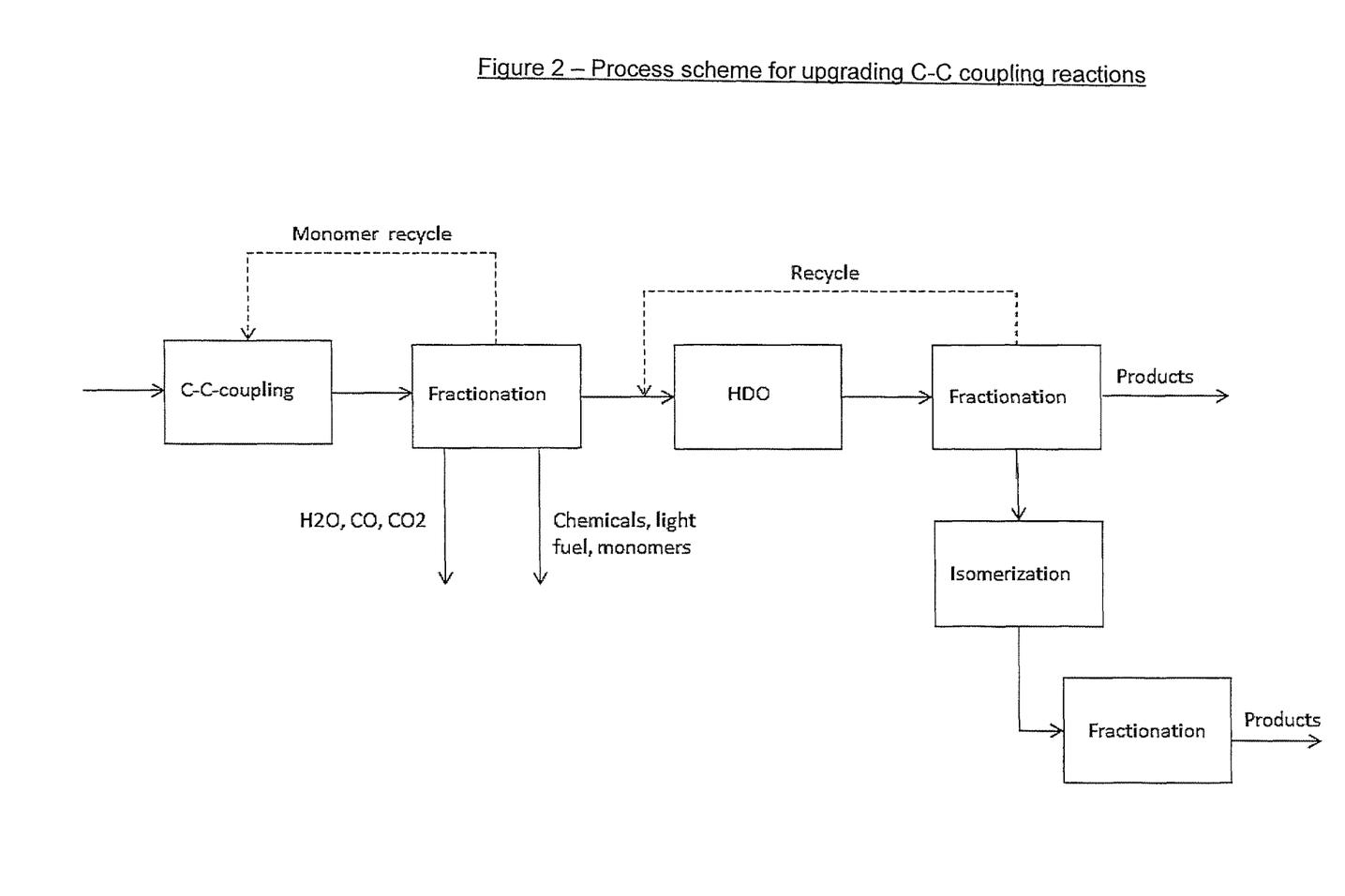
FIG. 2 shows an overview of a possible process scheme for further upgrading the products from the C-C-coupling reactions, according to an exemplary aspect.
Figure 3:
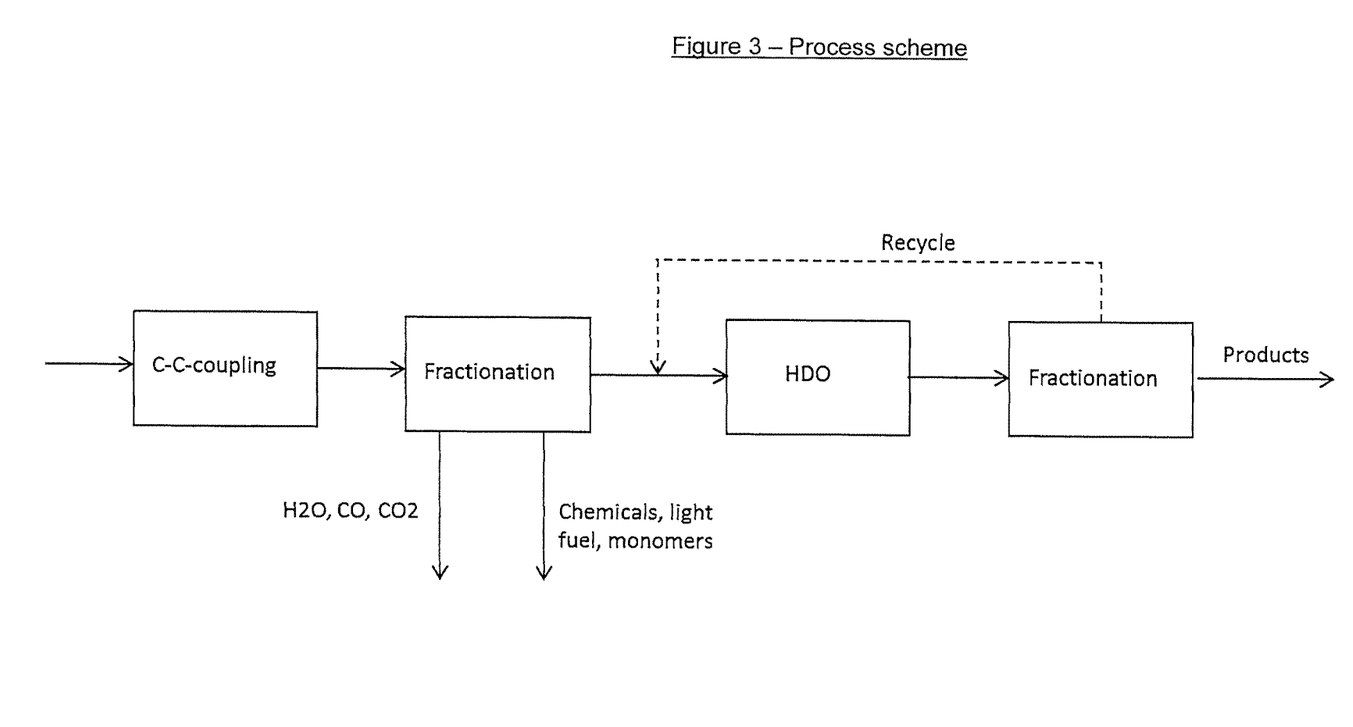
FIG. 3 shows an overview of a possible process scheme for preparing and upgrading the products from the C-C-coupling reactions, according to an exemplary aspect.

The ketoacid Levulinic acid (LA, 4-oxopentanoic acid) is one of many platform molecules that may be derived from biomass. It may be produced from both pentoses and hexoses of lignocellulosic material (see FIG. 1) at relatively low cost. Some of the advantages and drawbacks of using levulinic acid as a platform molecule relates to the fact that it is considered to be a reactive molecule due to both its keto and acid functionality.

Esters of levulinic acid have been suggested as fuel components as well as cold flow additives in diesel fuels, and, for example, the methyl and ethyl esters have been used as additives in diesel fuel. Gamma-valerolactone (GVL), which may be obtained by reduction of levulinic acid, has been used as a fuel additive in gasoline. Further reduction of GVL to 2-methyltetrahydrofuran (MTHF) provides a product that may be blended with gasoline of up to 60%. Alkyl valerates produced from levulinic acid have also been suggested as biofuels.

Levulinic acid has also been used for the production of liquid hydrocarbon fuels by a number of catalytic routes, including a method of producing a distribution of alkenes, the distribution centered around $C_{12}$, involving converting aqueous GVL in a first reactor system to butenes followed by oligomerization in a second reactor over an acidic catalyst (for example, Amberlyst® 70).

GB 601,922 (to John George Mackay Bremner) discloses the preparation of methyl vinyl ketone by heating i.a. levulinic acid in the vapour phase at a temperature of from 450° C. to 650° C.

Consequently, there is a need for additional processes for upgrading levulinic acid and other ketoacids to higher molecular weight compounds, which are suitable for use as, for example, fuel or heavy oil components or chemicals or as components in the production of fuel or heavy oil components or chemicals. For example, there is a need for such additional processes, which reduce the processing costs by, for example, improving the yield of the desired components or chemicals and/or improving the life time of the catalyst.

SUMMARY

The present disclosure was made in view of the prior art described above, and one of the objects of the present disclosure is to provide methods that enable upgrading of ketoacids such as levulinic acid to higher molecular weight compounds.

Another object of the present disclosure is to provide the upgrade of ketoacids to higher molecular weight compounds in good yield and at low processing costs.

To address the problem, an aspect of the present disclosure provides a method for increasing the molecular weight of ketoacids, the method comprising the steps of providing in a reactor a feedstock comprising at least one ketoacid; and subjecting the feedstock to one or more C-C-coupling reaction(s); wherein the C-C-coupling reaction(s) are conducted by heating the feedstock to a temperature of above 200° C., such as 200° C.-500° C. in the absence of a catalyst.

For example, the inventors of the present disclosure in a first aspect of the disclosure found that thermal treatment of a ketoacid feedstock at temperatures between 200-500° C. in the absence of a catalyst increases the molecular weight of the ketoacids to allow the isolation of compounds suitable for use as fuel or heavy oil components or chemicals; or as starting compounds for such products. Conducting the C-C-coupling reactions in the absence of a catalyst can also have the advantage that processing costs are lower than other methods in the art employing catalysts.

In some embodiments, the feedstock is heated to a temperature of 205-400° C., such as a temperature of 245-350° C.

In some embodiments, the feedstock is heated to a temperature, which is a range based on the highest boiling ketoacid of the at least one ketoacid, the lower end of the range being calculated as the boiling point temperature of the highest boiling ketoacid at atmospheric pressure minus 30° C., and the higher end of the range being calculated as the boiling point temperature of the highest boiling ketoacid at atmospheric pressure plus 100° C.

In some embodiments, the C-C-coupling reaction(s) are conducted mainly in the liquid phase.

In some embodiments, the C-C-coupling reaction(s) are conducted in a single reactor.

In some embodiments, the C-C coupling reaction(s) are conducted at a pressure of between 10-100 bar, such as a pressure of between 10-50 bar.

In some embodiments, the at least 60 wt-% of the feedstock comprises a ketoacid.

In some embodiments, the feedstock comprises a ketoacid and/or esters thereof.

In some embodiments, the feedstock comprises levulinic acid.

In another aspect of the present disclosure, a C-C-coupling reaction product obtainable by the methods according to the present disclosure is provided.

In another aspect of the present disclosure, a C-C-coupling reaction product comprising 4-methyl-6-oxonon-4-enedioic acid and 2,5,8 trioxo-nonane is provided.

In another aspect of the present disclosure, a method for producing hydrocarbons, the method comprising subjecting the C-C-coupling products of the present disclosure to a hydrodeoxygenation step and optionally an isomerisation step is provided.

In some embodiments, the hydrodeoxygenation step is conducted in the presence of a hydrodeoxygenation catalyst comprising a hydrogenation metal on a support.

In some embodiments, the metal of the hydrodeoxygenation catalyst is selected from the group consisting of one or more of: Pd, Pt, Ni, Co, and Mo.

In some embodiments, the isomerization step is conducted in the presence of a isomerization catalyst.

In some embodiments the isomerization catalyst is a noble metal bifunctional catalyst, for example, selected from the group consisting of one or more of: Pt-SAPO, and Pt-ZSM.

In another aspect of the present disclosure, a hydrocarbon product obtainable by the methods according to the present disclosure is provided.

In another aspect of the present disclosure, a hydrocarbon composition comprising a gasoline fraction, where the gasoline fraction comprises more than 40 wt % of a mixture of cyclopentanes and cyclohexanes having a total number of carbon atoms between 6 and 11 is provided.

In some embodiments, the mixture of cyclopentanes and cyclohexanes comprise at least 15 wt % of 1-methyl-2-propyl-cyclopentane and/or at least 2 wt % of 1-ethyl-4-methyl-cyclohexane.

In some embodiments, the mixture of cyclopentanes and cyclohexanes comprise at least 5 wt % of C10-cyclopentanes and/or at least 5 wt % of C10-cyclohexanes.

BRIEF DESCRIPTION OF THE DRAWINGS

Other features and advantages of the present disclosure will become apparent to those skilled in the art upon reading the detailed description of the embodiments in conjunction with the accompanying drawings, wherein.

DETAILED DESCRIPTION

In describing the embodiments of the disclosure, specific terminology will be resorted to for the sake of clarity. However, the disclosure is not intended to be limited to the specific terms so selected, and it is understood that each specific term includes all technical equivalents which operate in a similar manner to accomplish a similar purpose.

One of the challenges in increasing the molecular weight of ketoacids by catalytic C-C-coupling reactions such as ketonization reactions is the high reactivity of the product intermediates, which results in too high degree of oligomerization of the starting components. The inventors have surprisingly found out that, for example, several compounds which are known to be formed in catalytic C-C-coupling reactions can be produced by thermal treatment of a levulinic acid in the absence of a catalyst.

For example, the inventors have found that thermal treatment of levulinic acid at a temperature of above 200° C. without any added catalyst produces 4-methyl-6-oxonon-4enedioic acid, which may be formed from an aldol condensation reaction of two molecules of levulinic acid. The inventors have also found that the thermal treatment of levulinic acid without any added catalyst produces 2,5,8-trioxo-nonane, which is a ketonization reaction product of levulinic acid.

2,5,8 trioxo-nonane 4-methyl-6-oxonon-4-enedioic acid

Without wanting to be bound by any particular theory, it is considered that at temperatures above 200° C., the carboxylic acid group of levulinic acid functions as a catalytically active part and enables levulinic acid to function as catalyst in the C-C-coupling reactions.

The disclosure is based on the finding that the ketoacids such as levulinic acid can undergo various C-C-coupling reactions such as ketonization and aldol condensation reactions by subjecting the ketoacids to thermal treatment without any added catalyst at temperatures of above 200° C. Consequently, the molecular weight of ketoacids can be increased with thermal treatment without added catalyst to obtain compounds suitable for use as fuel or heavy oil components or chemicals or as starting compounds for the production of fuel or heavy oil components or chemicals. For example, the thermal treatment can be controlled so as to give the desired products in a useful yield without resulting too much in uncontrollable polymerization reactions to products not suitable as, for example, liquid fuel components.

Conducting the C-C-coupling reactions without any added catalyst has the significant advantage that the processing costs are significantly lower than in methods known from the related art.

Accordingly, in one aspect of the present disclosure is a method for increasing the molecular weight of ketoacids, the method comprising the steps of providing in a reactor a feedstock comprising at least one ketoacid; and subjecting the feedstock to one or more C-C-coupling reaction(s); wherein the C-C-coupling reaction(s) are conducted by heating the feedstock to a temperature of above 200° C., such as 200° C.-500° C. in the absence of a catalyst.

The present disclosure relates to, for example, a method for increasing the molecular weight of ketoacids.

Ketoacids are organic molecules that have both a keto function (>C=O) as well as a carboxylic acid (COOH) or carboxylate (COO⁻) function. In the present specification, special forms of ketoacids include embodiments where the keto function is an aldehyde (CH=O), and in some embodiments the keto functionality may not be an aldehyde.

In some embodiments, the ketoacids may also comprise esters of such ketoacids, where the carboxylic acid group is esterified with an alkyl substituent. Suitable esters of the ketoacid include esters with $C_1$-$C_{25}$-straight chain and branched alkanols with at least one hydroxyl function, such as 1, 2, 3, 4, 5, 7, 8, 9, 10 hydroxy functions, including, for example, methanol, ethanol, propanol, butanol, pentanol, hexanol, heptanol, octanol, nonanol, decanol, undecanol, dodecanol, and their isomers. Glycols (such as ethylene glycol, propylene glycol), glycerol, sorbitol, glucitol as well as other carbohydrate derived polyols can be included. In some embodiments, the alkanol has one, two or three hydroxyl functionalities. In some embodiments, the esters are selected from the following alcohols: methanol, ethanol, ethylene glycol, and glycerol. The alkyl substituent may additionally be unsaturations, such as double or triple bonds, and the alkyl substituent may be unsubstituted or substituted.

In some embodiments, the ketoacid is an alpha-ketoacid (such as pyruvic acid, oxaloacetic acid and alpha-ketoglutaric acid), beta-ketoacid (such as acetoacetic acid), gamma-ketoacid (such as levulinic acid), or delta-ketoacid. The ketoacid may have more than one keto functionality, and more than one carboxylic acid function. In some embodiments, the ketoacid only has one keto functionality and one carboxylic acid functionality.

Scheme 1

Scheme 1 illustrates exemplary ketoacids according to the present disclosure, for example where n and m are integers each selected independently of each other from the list consisting of 0, 1, 2, 3, 4, 5, 6, 7, 8, 9, 10, for example in exemplary embodiments where the ketoacid is levulinic acid (m=2, n=0).

The feedstock may comprise as the major component one or more ketoacids, for example, in some embodiments at least 30% such as at least 60%, at least 70%, at least 80%, at least 90%, at least 95% or 100% of the feedstock comprises a ketoacid. The feedstock may be obtained from processing of lignocellulosic material, and such processed material may be used directly, or purified to varying degrees before being used as a feedstock in the method of the present disclosure. In some embodiments, the feedstock comprises levulinic acid, and in some embodiments, the levulinic acid may be combined with one or more other ketoacids. In other embodiments, the feedstock comprises a mixture of levulinic acid in combination with angelica lactones, such as at least 10% of levulinic acid and at least 10% of angelica lactones.

In addition to ketoacids, the feedstock may in some embodiments also contain derivatives, such as aldehydes, for example, as furfural or hydroxymethylfurfural.

In some embodiments of the present disclosure, the feedstock comprises levulinic acid.

The feedstock may contain water, and in some embodiments, the feedstock has a water content of 15 wt % or less. In some embodiments, the water content is as low as possible, for example, a water content of 10 wt % or less, such as 5 wt % or less, or 1 wt % or less, for example, no water is present. In some embodiments, no external water is added during the C-C-coupling reaction(s), although internal water is produced in some condensation reactions.

In some embodiments, external water is added in an amount of 0.1wt % to 10wt % either to the feedstock and/or during the reactions, as, for example, steam.

In some embodiments, the feedstock is fed into in a single reactor, or single reactor bed, for example a CSTR reactor or a trickle bed reactor. The reactor can be pressurized, and can accommodate the feedstock. The reactor can have means, such as one or more inlets and/or outlets, for example, to enable adding/withdrawing of feedstock. Means for controlling the pressure and temperature can also be present.

In some embodiments, the molecular weight of the ketoacids in the feedstock are increased at least 40% or more. In some embodiments, the molecular weight is increased to between 150 and 1500 g/mol, such as 200 and 500 g/mol. In some embodiments, where the ketoacid is a $C_4$-$C_7$-ketoacid, the molecular weight is increased to corresponding molecules having a $C_{13}$-$C_{50}$ carbon chain, such as a $C_{13}$-$C_{30}$ carbon chain. In some embodiments, more than 50 wt % of the reaction product may be determined to belong to the group containing trimerization, tetramerization, pentamerization, and hexamerization products. By trimerization, tetramerization, pentamerization and hexamerization products is meant reaction products relating to three, four, five and six molecules of one or more of ketoacids being coupled together. In the case of a feedstock other derivatives, such as in some feedstocks of biomass origin, which comprises other derivatives in addition to ketoacids, the trimerization, tetramerization, pentamerization, and hexamerization products may additionally contain mixed C-C-coupling products comprising one or more ketoacids and derivatives thereof. The trimerization, tetramerization, pentamerization, and hexamerization products are derived from at least one ketoacid, such as at least two ketoacids, at least three ketoacids, at least four ketoacid, at least five ketoacids, at least six ketoacids.

In the present disclosure, for example, the molecular weight of the keto acids are increased through one or more C-C-coupling reaction(s). Many C-C-coupling reactions are known in the art, and the skilled person would be able to identify such C-C-coupling reactions based on the reaction conditions provided. For example, the C-C-coupling reactions may be ketonization reactions or reactions proceeding through an enol or enolate intermediate. In some embodiments, C-C-coupling reactions are selected from the list comprising: aldol-type reactions and condensations, ketonizations, reactions where the C-C-coupling involves an alkene, as well as other oligomerization reactions. The C-C-coupling reactions may proceed with two identical molecules or may be a crossed reaction between two different molecules.

For example, the C-C coupling reaction(s) proceeds in the absence of a catalyst system. For example, it was found that subjecting the feedstock of the present disclosure to C-C-coupling reactions in the absence of a catalyst and at temperatures above 200° C. will increase the molecular weight of the ketoacids to allow the isolation of compounds suitable for use as fuel or heavy oil components or chemicals; or as starting compounds for such products. Conducting the C-C-coupling reactions in the absence of a catalyst also has the advantage that processing costs are lower than other methods in the art employing catalysts. For example, the thermal treatment can be controlled so as to give the desired products in a useful yield without resulting too much in uncontrollable polymerization reactions to products not suitable as, for example, liquid fuel components. While the ketoacids of the feedstock may themselves be considered to catalyse a number of C-C-coupling reactions, including the aldol reaction/condensation through auto-catalysis, the feedstock is in the present context not considered to be the catalyst system. In the context of the present disclosure, absence of a catalyst system is considered to be in the absence of a catalyst system in the solid phase.

For example, the inventors found that thermal treatment of a ketoacid feedstock (for example, levulinic acid) at temperatures between 200-500° C. in the absence of a catalyst increase the molecular weight of the ketoacids to allow the isolation of compounds suitable for use as fuel or heavy oil components or chemicals; or as starting compounds for such products. For example, the thermal treatment resulted in novel gasoline fractions with a high content of cyclopentane and cyclohexane compounds. Conducting the C-C-coupling reactions in the absence of a catalyst can also have the advantage that processing costs are lower than other methods in the art employing catalysts.

In some embodiments, the feedstock is heated to a temperature, which is a range based on the highest boiling ketoacid of the at least one ketoacid, the lower end of the range being calculated as the boiling point temperature of the highest boiling ketoacid at atmospheric pressure minus 30° C., and the higher end of the range being calculated as the boiling point temperature of the highest boiling ketoacid at atmospheric pressure plus 100° C.

With reference to, for example, Levulinic acid (bp=245-246° C. @ 1 bar) it was found in the examples that a suitable temperature range for conversion to dimer and oligomer product could be effected around the boiling point of levulinic acid. For example, in some embodiments, where levulinic acid is the ketoacid, the temperature range could be from 215-216° C. to 345-346° C.

In some embodiments, the feedstock, such as levulinic acid, is heated to a temperature of 205-400° C., such as a temperature of 245-350° C.

For example, the reaction can suitably be performed for a time sufficient to convert the feedstock to C-C-coupling products. In some embodiments, the C-C-coupling reaction(s) will be conducted for a reaction time sufficient to convert 40 wt % of the feedstock to C-C-coupling products. The reaction time may vary depending on the type of reactor used, such as between 30 min and 240 minutes, for example, for 30-150 minutes. In some embodiments, where the feedstock comprise levulinic acid and/or esters thereof, the reaction time is between 30 min and 240 minutes calculated after the temperature has reached at least 200° C., such as at least 250° C.

In some embodiments, the C-C-coupling reaction(s) are conducted predominantly in the liquid phase, as opposed to the gaseous phase, meaning that the reaction is at least predominantly taking place on in the liquid phase. In some embodiments, the C-C-coupling reaction(s) are conducted entirely in the liquid phase.

In some embodiments, the C-C-coupling reaction(s) are conducted in a closed reactor. Performing the reactions in a closed reactor allows the feedstock to be heated above its boiling point temperature.

When the feedstock is heated to around the boiling point in a closed reactor, pressure can rise due to the vapor pressure of the feedstock. As the thermal C-C-coupling reactions proceed and generate $CO_2$ and water vapor, the pressure can increase further.

In some embodiments, the C-C coupling reaction(s) are conducted at a pressure of between 10-100 bar, such as a pressure of between 10-50 bar.

In some embodiments, the pressure can be controlled by pressurizing the reactor prior to heating using, for example, a gas behaving inertly to the thermal reactions, such as helium. By behaving inertly is considered that the gas does not to a major extent participate as a reaction member, for example, the inert gas participates as little as possible, such as not participate at all. For example, the gas is inert, but in some embodiments it is also exemplary for economic reasons to use cheaper gasses that may not entirely behave inertly under the reaction conditions, such as air, $CO_2$ or water vapour.

The reactor can also be pressurized by the products of the condensation reactions by sealing the reactor, heating the feedstock, thereby allowing the reactor to become pressurized by generation of $CO_2$ and water vapor from the reactions of the feedstock.

For example, the pressure may also be controlled, by venting excess gases if the pressure becomes too high. In some embodiments, the pressure is kept between 15 and 30 bar.

In another aspect of the present disclosure, a C-C-coupling reaction product obtainable by the method according to the present disclosure is provided. This product may be used as fuel or heavy oil components or chemicals or as intermediate components in production of fuel or heavy oil components or chemicals.

A C-C-coupling reaction product comprising 4-methyl-6-oxonon-4-enedioic acid and 2,5,8 trioxo-nonane is provided. In some embodiments, the C-C-coupling reaction product comprise at least 1 wt % of each of 4-methyl-6-oxonon-4-enedioic acid and 2,5,8 trioxo-nonane, and in some embodiments at least 5 wt % of the C-C-coupling reaction product comprise the compounds 4-methyl-6-oxonon-4-enedioic acid and 2,5,8 trioxo-nonane.

The C-C-coupling reaction products of the present disclosure and obtainable by the methods of the present disclosure may, if desired, be further subjected to a hydrodeoxygenation (HDO) step to remove oxygen, which in some embodiments produce completely deoxygenated material. The produced hydrocarbons may be used as fuel or heavy oil components or chemicals or as starting components in the production of fuel or heavy oil components or chemicals. The hydrodeoxygenated products may also be further isomerized to isoparaffins in the presence of hydrogen.

An exemplary advantage of the present disclosure is that ketoacids produced from renewable materials can be upgraded to higher molecular weight compounds, which may be used as fuel or heavy oil components or chemicals or as starting components in the production of fuel or heavy oil components or chemicals.

The C-C-coupling reaction products may be fractionated to remove potential unreacted ketoacid monomers and other light components such as water and $CO_2$ formed in the C-C-coupling reactions. The fractionation can be conducted by any suitable means such as distillation. The unreacted ketoacid monomer may optionally be recycled and combined with the feed of the first reactor.

Accordingly, another aspect of the present disclosure involves a method for production of hydrocarbons, the method comprising subjecting the C-C-coupling reaction products obtained to a hydrodeoxygenation step in the presence of a hydrodeoxygenation (HDO) catalyst. In some embodiments, the HDO catalyst comprises a hydrogenation metal on a support, such as, for example, a HDO catalyst selected from a group consisting of Pd, Pt, Ni, Co, Mo, or any combination of these. The hydrodeoxygenation step may, for example, be conducted at a temperature of 100-500° C. and at a pressure of 10-150 bar.

Water and light gases may be separated from the HDO product with any suitable means such as distillation. After the removal of water and light gases, the HDO product may be fractionated to one or more fractions suitable for use as gasoline, aviation fuel, diesel or heavy oil components. The fractionation may be conducted by any suitable means, such as distillation. Optionally, part of the product of the HDO step may be recycled and combined to the feed of the HDO reactor.

The product of the hydrodeoxygenation step may also be subjected to an isomerization step in the presence of an isomerization catalyst and hydrogen. Both the hydrodeoxygenation step and isomerisation step may be conducted in the same reactor. In some embodiments, the isomerization catalyst is a noble metal bifunctional catalyst, for example, Pt-SAPO or Pt-ZSM-catalyst. The isomerization step may, for example, be conducted at a temperature of 200-400° C. and at a pressure of 20-150 bar.

It is exemplary that only a part of the HDO product is subjected to an isomerization step, for example, the part of HDO product which is subjected to isomerization may be the heavy oil fraction boiling at or above temperature of 300° C.

The hydrocarbon product obtainable from the hydrodeoxygenation and/or the isomerization step may be used as fuel or heavy oil components or chemicals or as intermediate components in production of fuel or heavy oil components or chemicals.

For example, the choice of subjecting HDO product to isomerization is highly dependable of the desired properties of the end products. Aromatic compounds are desirable if the end product is aviation fuel since the Jet fuel standard requires a certain amount of aromatic compounds to be present in aviation fuel. Since the isomerization can decompose aromatic and cyclized compounds, the HDO product would not necessarily be subjected to isomerization step if the object is to produce aviation fuel. On the other hand, it can be advantageous to minimize the amount of aromatic compounds in diesel fuel fractions since the aromatics decrease the cetane number of diesel.

For example, it was found that levulinic acid, which has undergone thermal treatment according to the present disclosure, and further been subjected to a HDO step comprise a novel gasoline fraction with a high cyclopentane and cyclohexane content.

In some embodiments, the novel gasoline fraction has a content of acyclic paraffins (straight- and branched-chain paraffins) below 30 wt % and a content of cyclopentane and cyclohexane compounds of more than 30 wt %, for example, more than 40 wt %.

The gasoline fraction may in some embodiments be the C1-C12 fraction and/or the fraction having an initial boiling point (IBP) of about 30° C. and a final boiling point (FBP) of about 205° C. or for example until a FBP of about 180° C.

For example, as shown in example 8, a large fraction of the hydrocarbon composition produced after the HDO step is in the gasoline fraction. The gasoline fraction was subjected to a PIONA analysis, which identifies Paraffins, Iso-paraffins, Olefins, Naphthenes, Aromatics and Oxygenates.

For example, more than 40 wt % of the gasoline fraction can comprise a mixture of cyclopentanes and cyclohexanes having a total number of carbon atoms between 6 and 11. For example, in some embodiments, the mixture of cyclopentanes and cyclohexanes comprise at least 5 wt % of C10-cyclopentanes and/or at least 5 wt % of C10-cyclohexanes.

For example, the cyclopentanes and cyclohexanes are monocyclic, whereas the naphthenes are not exclusively monocyclic. C10-cyclopentanes and C10-cyclohexanes means that there is 10 carbons in the compound, where five of those carbons make out the cyclopentane ring in C10-cyclopentanes, and where six of those carbons make out the cyclohexane ring in C10-cyclohexanes.

For example, closer analysis of the cyclopentanes revealed that it comprised more than 15 wt % 1-methyl-2-propyl-cyclopentane, which can be used as a solvent molecule.

For example, closer analysis of the cyclohexanes revealed that it comprised more than 2 wt %, for example, more than 4 wt % of 1-ethyl-4-methyl-cyclohexane, which can also be used as a solvent molecule.

When describing the embodiments of the present disclosure, the combinations and permutations of all possible embodiments have not been explicitly described. Nevertheless, the mere fact that certain measures are recited in mutually different dependent claims or described in different embodiments does not indicate that a combination of these measures cannot be used to advantage. The present disclosure envisages all possible combinations and permutations of the described embodiments.

The terms "comprising", "comprise" and comprises herein are intended by the inventors to be optionally substitutable with the terms "consisting of", "consist of" and "consists of", respectively, in every instance.

EXAMPLES

The Examples 1-7 show that it is possible to increase the molecular weight of levulinic acid by C-C-coupling reactions conducted at a temperature of above 200° C. without any added catalyst. The examples also show that the C-C-coupling reaction product of levulinic acid can be further processed to hydrocarbons having a boiling point range of typical fuel or heavy oil components such as naphta, kerosene and diesel by subjecting the C-C-coupling reaction product of levulinic acid to hydrodeoxygenation reactions in the presence of a typical HDO catalyst and hydrogen.

The examples also show that the hydrocarbon products having a boiling point range of typical fuel or heavy oil components such as naphta, kerosene and diesel produced in the experiments have excellent cold properties without further isomerization treatment.

Gel Permeation Chromatography

The oil product distributions presented in tables 1-7 were obtained by gel permeation chromatography using refractive index as the detector and tetrahydrofuran as the eluent. A peak is present where levulinic acid eluted. Elution times starting with the levulinic acid peak, and elution times after levulinic acid were ascribed to monomers, i.e. non-C-C-coupled products, which could be smaller molecular weight compounds compared to levulinic acid. For products eluting earlier than the levulinic acid, two peaks could be seen, one which could be ascribed to dimers of levulinic acid based on GC-MS, and a broader peak, which could be ascribed to oligomers derived from three or more molecules of levulinic acid. The Monomer, Dimer and Oligomer columns in tables 1-7 are based on the area under the peaks in the GPC chromatograms.

Examples 1-5

Increasing the Molecular Weight of Levulinic Acid by C-C-coupling Reactions

Example 1

Levulinic acid derived from biomass was heat treated in an autoclave reactor for 4 hours. Treatment was carried out at a fixed temperature of 250° C. In this example, the decomposition products from the condensing reactions were allowed to increase pressure as the test run proceeded. At the end of the test run pressure had increased to 75 bars. Reactor was allowed to cool to condense vaporized products. After cooling to 25° C., the pressure was 30 bars. Gaseous components were analyzed to be >95% of $CO_2$ with minor amount of hydrocarbons and CO. Oil distribution in samples retrieved from the reactor at 60 minutes, 120 minutes and 240 minutes are presented in Table 1. Oil product distribution was obtained by gel permeation chromatography.

TABLE 1

Process conditions and oil product distribution.

| Process conditions | | | Oil composition | | | |
|---|---|---|---|---|---|---|
| Temp. ° C. | Pressure bar | Sample | Monomer area-% | Dimer area-% | Oligomer area-% | Experiment |
| 250 | 12 | 2 | 72 | 17 | 11 | EX 1 |
| 250 | 21 | 3 | 56 | 17 | 27 | EX 1 |
| 250 | 74 | 4 | 43 | 17 | 40 | EX 1 |

Example 2

Levulinic acid derived from biomass was heat treated in an autoclave reactor for 3 hours. Treatment was carried out at a fixed temperature of 275° C. In this example, the decomposition products from the condensing reactions were allowed to increase pressure to 20 bars. Excess gas was removed via vessel gas outlet.

Oil distribution in samples retrieved from reactor at 60 minutes, 120 minutes and 240 minutes is presented in Table 2. Oil product distribution was obtained by gel permeation chromatography.

TABLE 2

Process conditions and oil product distribution.

| Process conditions | | | Oil composition | | | |
|---|---|---|---|---|---|---|
| Temp. ° C. | Pressure bar | Sample | Monomer area-% | Dimer area-% | Oligomer area-% | Experiment |
| 275 | 20 | 2 | 69 | 16 | 15 | EX 2 |
| 275 | 20 | 3 | 53 | 17 | 30 | EX 2 |
| 275 | 20 | 4 | 28 | 16 | 56 | EX 2 |

Figure 4:
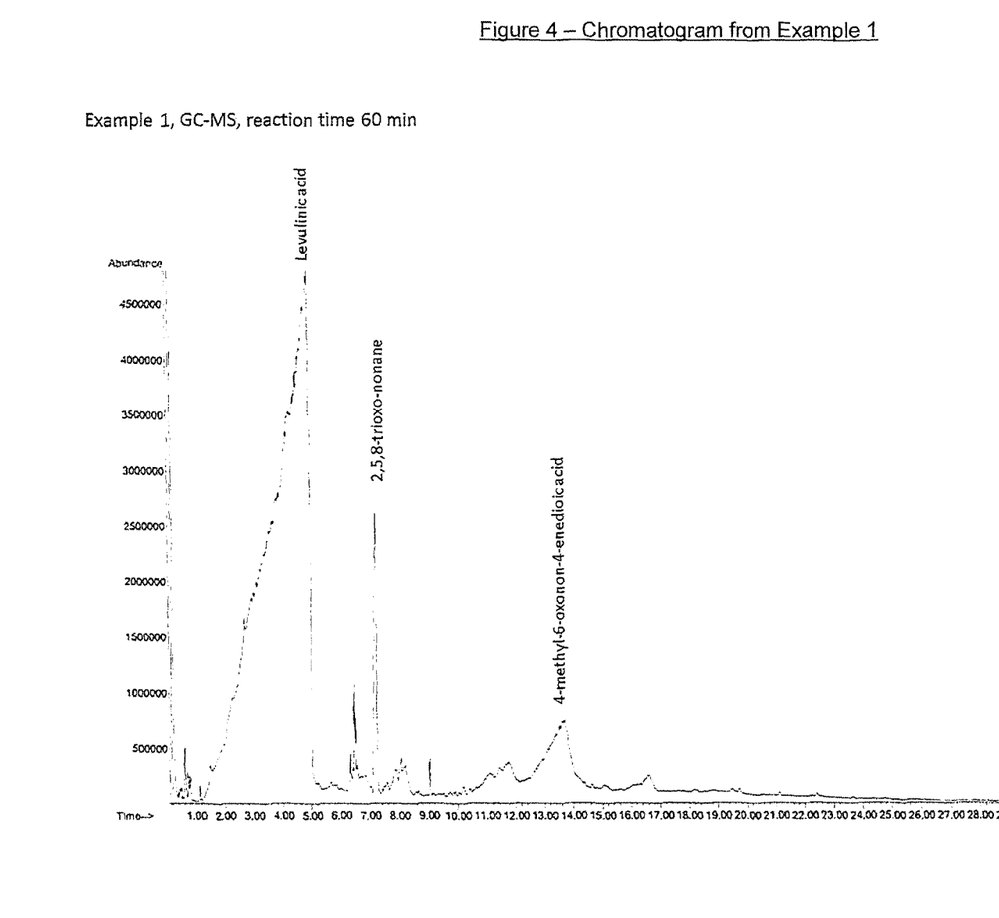
FIG. 4 shows a gas chromatogram from example 1.

A GC-MS analysis was performed on the sample retrieved from the reactor at 60 minutes, see FIG. 4. Due to the multiple and complex reaction chemistry only some compounds are shown in the chromatogram.

Example 3

Levulinic acid derived from biomass was heat treated in an autoclave reactor for 3 hours. Treatment was carried out at a fixed temperature of 300° C. In this example, the decomposition products from the condensing reactions were allowed to increase pressure to 20 bars. Excess gas was removed via vessel gas outlet.

Oil distribution in samples retrieved from vessel at 60 minutes, 120 minutes and 180 minutes is presented in Table 3. Oil product distribution was obtained by gel permeation chromatography.

TABLE 3

Process conditions and oil product distribution.

| Process conditions | | | Oil composition | | | |
|---|---|---|---|---|---|---|
| Temp. ° C. | Pressure bar | Sample | Monomer area-% | Dimer area-% | Oligomer area-% | Experiment |
| 300 | 20 | 2 | 21 | 19 | 60 | EX 3 |
| 300 | 20 | 3 | 8 | 15 | 77 | EX 3 |
| 300 | 20 | 4 | 5 | 14 | 81 | EX 3 |

Example 4

Levulinic acid derived from biomass was heated in a distillation flask for 2.5 hours. Treatment was carried out at a fixed temperature of 200° C. Sample was purged with nitrogen gas to remove air from system and ease evaporation of decomposed products. In this example decomposition products were distillated with average speed of 17% of distillate pr. hour. Excess gas was removed via vessel gas outlet.

Process conditions, process yields and oil distribution of collected distillate and bottom product are presented in Table 4. Oil product distribution was obtained by gel permeation chromatography.

TABLE 4

Process conditions, process yields and oil product distributions of distillate and bottom fractions, Experiment 4.

| | Yields | | Oil composition, distillate | | | Oil composition, bottom | | |
|---|---|---|---|---|---|---|---|---|
| Temp. ° C. | Distillate wt-% | Bottom wt-% | Monomer area-% | Dimer area-% | Oligomer area-% | Monomer area-% | Dimer area-% | Oligomer area-% |
| 205 | 24 | 70 | 99 | 1 | 0 | 79 | 19 | 2 |

The distillate fraction from experiment 4 was analysed with HPLC to determine monomer composition in more detail. Distillate contained 29 wt-% of angelica lactone and 43 wt-% of levulinic acid.

Example 5

Levulinic acid derived from biomass was heated in a distillation flask for 2 hours. Treatment was carried out at a fixed temperature of 245° C. Sample was purged with nitrogen gas to remove air from system and ease evaporation of decomposed products. In this example, decomposition products were distillated with average speed of 6% of distillate per hour. Excess gas was removed via vessel gas outlet.

Process conditions, process yields and oil distribution of collected distillate and bottom product are presented in Table 5. Oil product distribution was obtained by gel permeation chromatography.

TABLE 5

Process conditions, process yields and oil product distributions of distillate and bottom fractions. Experiment 5.

| Temp. °C. | Yields | | Oil composition, distillate | | | Oil composition, bottom | | |
|---|---|---|---|---|---|---|---|---|
| | Distillate wt-% | Bottom wt-% | Monomer area-% | Dimer area-% | Oligomer area-% | Monomer area-% | Dimer area-% | Oligomer area-% |
| 245 | 16 | 79 | 95 | 3 | 2 | 54 | 25 | 21 |

The distillate product formed two separately layered fractions, an organic layer and a water layer. The fractions were separated with tap funnel. 30 wt-% of the distillate was $H_2O$, with <10% of dissolved organic compounds. The organic fraction of the distillate was analyzed with HPLC to determine monomer composition in more detail. The distillate fraction contained 79 wt-% of angelica lactone and 1 wt-% of levulinic acid.

Figure 5:
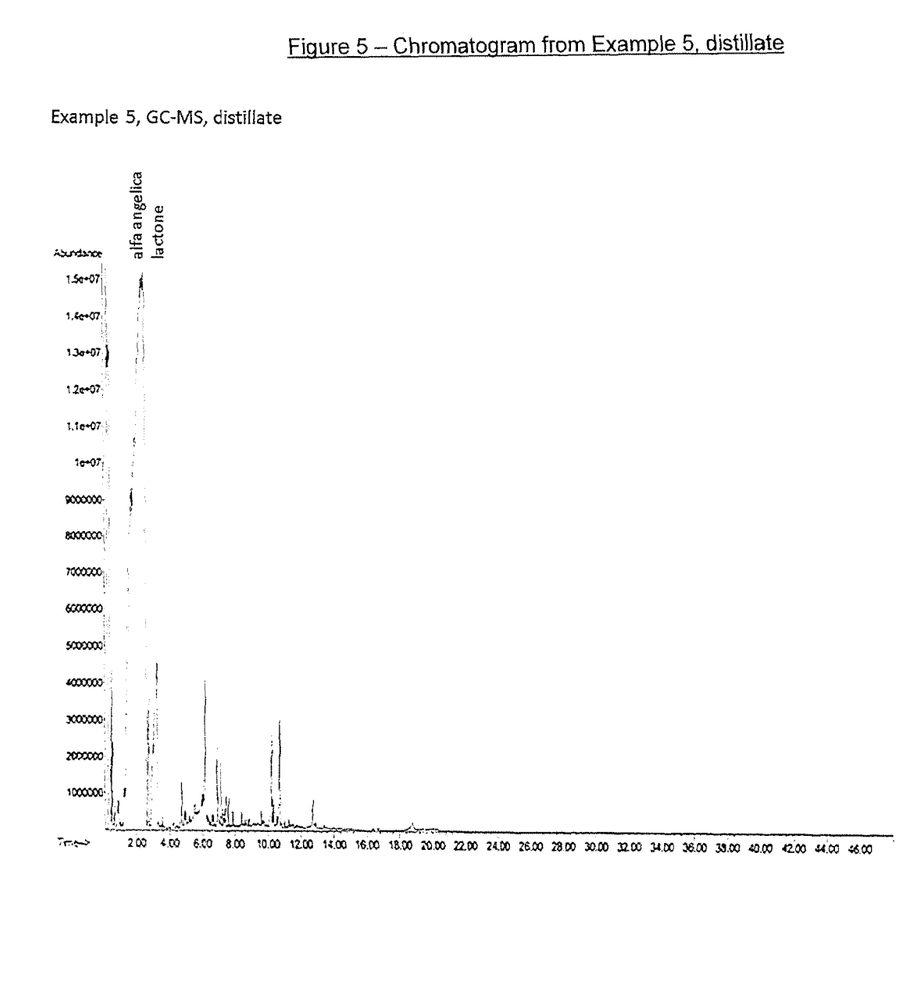
FIG. 5 shows a gas chromatogram from example 5, distillate.
Figure 6:
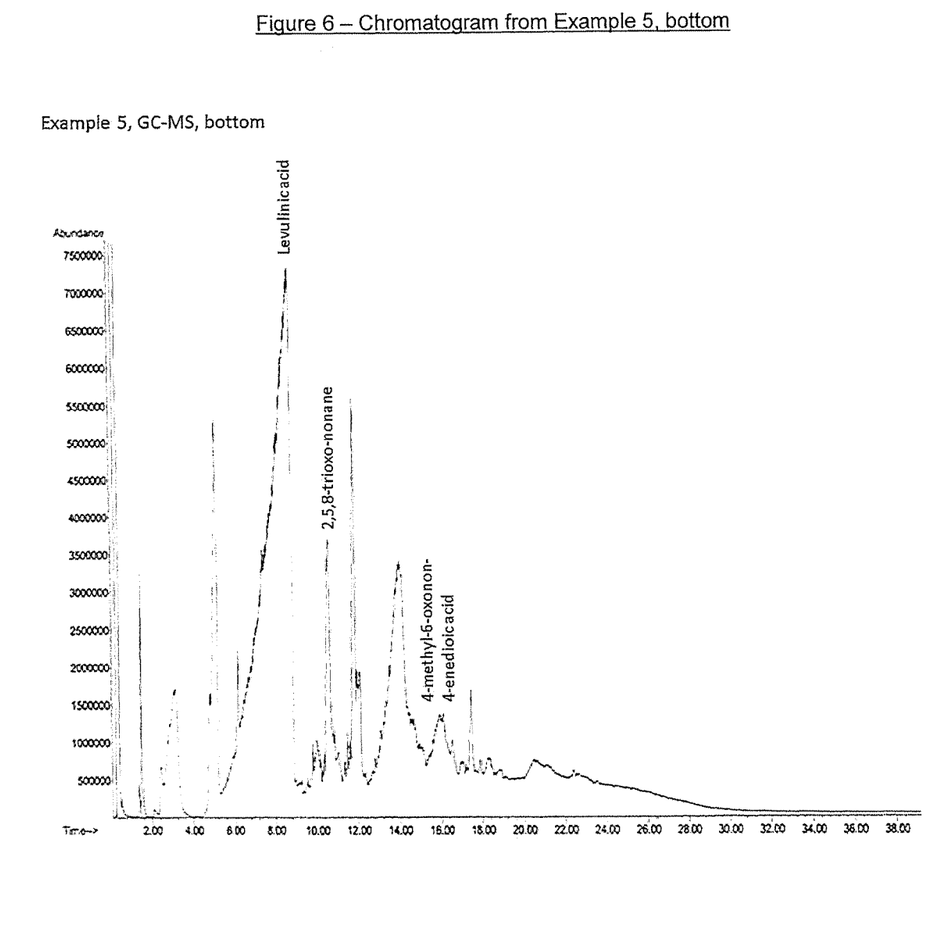
FIG. 6 shows a gas chromatogram from example 5, bottom.

A GC-MS analysis was performed to the distillate and bottom product. A chromatogram of the distillate product is shown in FIG. 5, and the bottom product is shown in FIG. 6. Due to the multiple and complex reaction chemistry only some compounds are shown in the chromatogram.

Examples 6-7

Method for Producing Hydrocarbons from C-C-coupling Reaction Products of Levulinic Acid Example 6

In this example levulinic acid was subjected to reactive distillation in a batch distillation apparatus and the formed bottom product was separated with vacuum distillation. The bottom product was subjected to hydrodeoxygenation reactions to remove heteroatoms from produced levulinic acid monomers.

Levulic acid derived from biomass was heated in a distillation flask for 2 hours. Treatment was carried at fixed temperature of 245° C. The decomposition products were distillated with average speed of 8% of distillate per hour. Excess gas was removed via vessel gas outlet.

Process conditions, process yields and oil distribution of collected distillate product and bottom is presented in Table 6. Oil product distribution was obtained by gel permeation chromatography.

TABLE 6

Process conditions, process yields and oil product distribution of obtained distillate and bottom fractions. Experiment 6.

| Temp. °C. | Yields | | Oil composition, distillate | | | Oil composition, bottom | | |
|---|---|---|---|---|---|---|---|---|
| | Distillate wt-% | Bottom wt-% | Monomer area-% | Dimer area-% | Oligomer area-% | Monomer area-% | Dimer area-% | Oligomer area-% |
| 245 | 15 | 83 | 97 | 2 | 1 | 74 | 20 | 6 |

The organic distillate from experiment 6 was analysed with HPLC to determine monomer composition in more detail. The distillate contained 17 wt-% of angelica lactone and 38 wt-% of levulinic acid.

The bottom fraction obtained from reactive distillation (Experiment 6) was further distilled at reduced pressure to separate monomers from oligomers. The product distributions of the distillate and bottom fractions of this distillation are presented in Table 7. The product distribution was obtained by gel permeation chromatography.

TABLE 7

Distillation conditions, process yields and product distribution of distillated fractions. Experiment 6.1.

| Distillation conditions | | Yields | | Oil composition, distillate | | | Oil composition, bottom | | |
|---|---|---|---|---|---|---|---|---|---|
| Temperature °C. | Pressure kPa | Distillate wt-% | Bottom wt-% | Monomer area-% | Dimer area-% | Oligomer area-% | Monomer area-% | Dimer area-% | Oligomer area-% |
| 180 | 1 | 84 | 16 | 95 | 5 | 0 | 0 | 80 | 20 |

Figure 7:
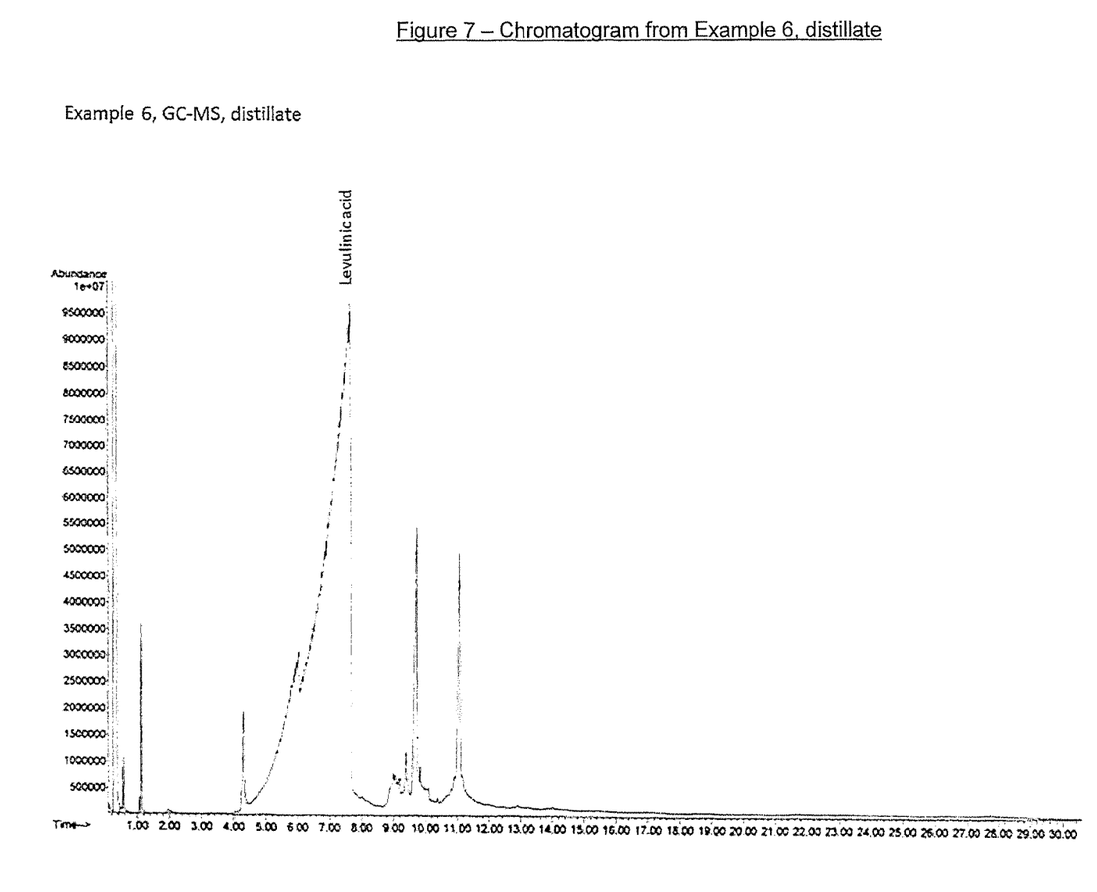
FIG. 7 shows a gas chromatogram from example 6, distillate.
Figure 8:
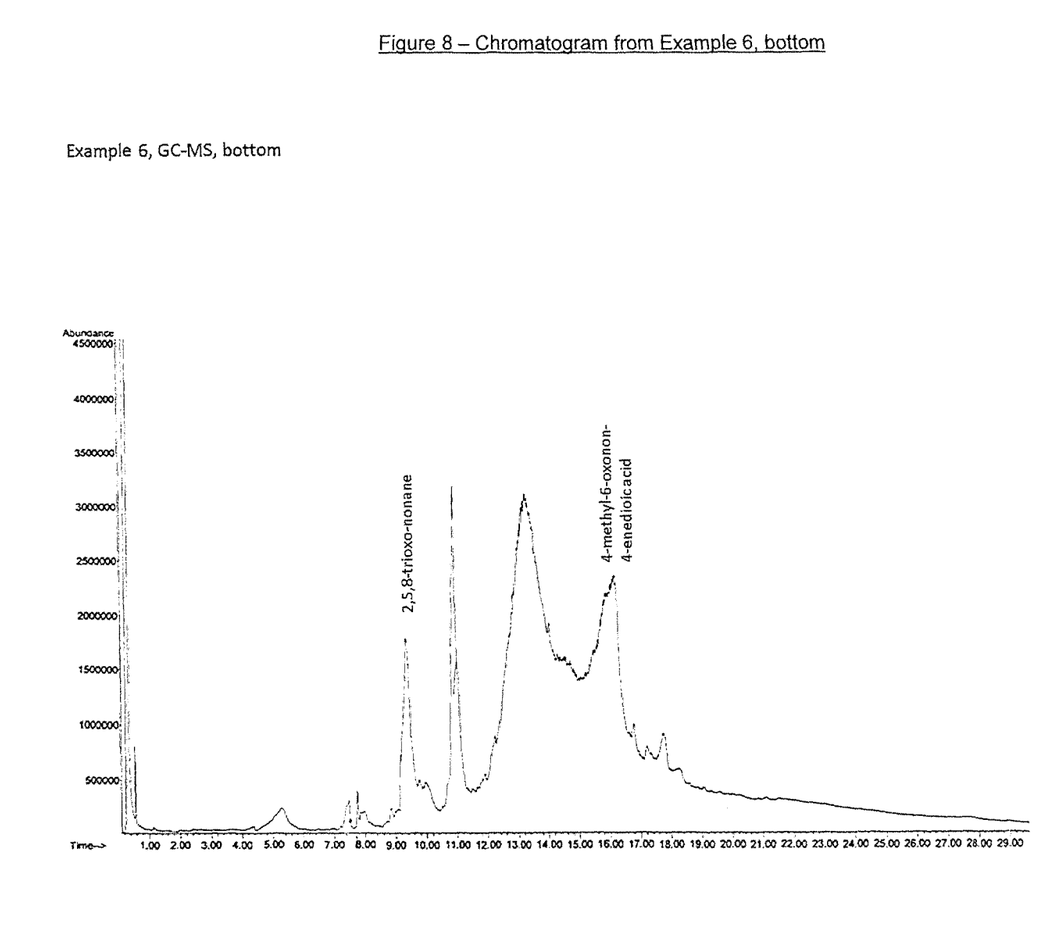
FIG. 8 shows a gas chromatogram from example 6, bottom.

Composition of the bottom product and the distillate was analyzed with GC-MS. A chromatogram of the distillate product is shown in FIG. 7 and of the bottom in FIG. 8. Due to the multiple and complex reaction chemistry only some compounds are shown in the chromatograms.

The bottom product obtained from the distillation (Experiment 6.1) was subjected to hydrodeoxygenation reactions to remove heteroatoms and to stabilize the oil product.

The hydrodeoxygenation reactions were conducted in presence sulphided NiMo on alumina carrier catalyst at a temperature of 310-320° C. and under a pressure of 0.5 MPa, using hydrogen to hydrocarbon ($H_2$/HC) ratio of 2500 Nl/l and weight hourly space velocity (WHSV) of 0.3 $h^{-1}$. WHSV and hydrogen to hydrocarbon ratio was calculated based on the amount of tested oil fed in reactor. Process conditions and process yields are presented in Table 8. Oil product distribution is presented in Table 9. Oil product boiling point distribution is obtained by GC-distillation (EN15199-2)

TABLE 8

Process conditions and process yields of hydrodeoxygenation.

| Catalyst | Reactor T, P | $H_2$/HC, WHSV | Experiment |
|---|---|---|---|
| NiMo + S | 310-320° C., 0.5 MPa | 2500, 0.3 | |
| Gas + $H_2O$ | | Oil | |
| 47 | | 53 | EX 6.2 |

TABLE 9

Oil product boiling point distribution.

| BP-180° C. weight-% | 180-360° C. weight-% | >360° C. weight-% | Experiment |
|---|---|---|---|
| 19 | 50 | 31 | EX 6.2 |

The oil product from experiment 6.2 was further distilled at reduced pressure to typical fuel fractions. The products however are not limited to these examples. Properties of the distilled oil product fractions are shown in Table 10.

TABLE 10

Properties of HDO product fractions.

| | | | Naphta/kerosene | Kerosene | Diesel/Process Oil |
|---|---|---|---|---|---|
| ENISO 12185 | Density 15° C. | kg/m³ | 788.9 | 871 | 931.8 |

TABLE 10-continued

Properties of HDO product fractions.

| | | | Naphta/kerosene | Kerosene | Diesel/Process Oil |
|---|---|---|---|---|---|
| ASTM D7689 | Cloud point | ° C. | Below −95 | Below −95 | −81.2 |
| ASTM D2887 | Boiling point ° C. | 10% | 129 | 166 | 282 |
| ASTM D2887 | Boiling point ° C. | 20% | 144 | 194 | 296 |
| ASTM D2887 | Boiling point ° C. | 30% | 146 | 216 | 307 |
| ASTM D2887 | Boiling point ° C. | 40% | 148 | 225 | 318 |
| ASTM D2887 | Boiling point ° C. | 50% | 150 | 236 | 329 |
| ASTM D2887 | Boiling point ° C. | 60% | 158 | 247 | 342 |
| ASTM D2887 | Boiling point ° C. | 70% | 167 | 261 | 357 |
| ASTM D2887 | Boiling point ° C. | 80% | 178 | 278 | 376 |
| ASTM D2887 | Boiling point ° C. | 90% | 215 | 299 | 402 |

Example 7

Levulinic acid derived from biomass was subjected to thermal treatment. Treatment was carried out in trickle bed reactor. Reactor was packed with coarse quartz sand sieved to particle size 1-3 mm. In this example, temperature and feed rate was altered. The reactor temperature was between 250 to 350° C. and feed rate was between 15 to 45 g/h and residence time of feed was between 0.6 to 2.1 $h^{-1}$. Process conditions and process yields are presented in Table 11.

Oil products (EX 7.1-7.8) obtained were distillated in laboratory with distillation device. Each sample was fractionated with cut point of 115° C. Yields from fractioning are presented in Table 11. The "Oil yield <115° C." fraction mainly comprised water.

Oil product (boiling at >115° C.) distributions are presented in table 12. Distribution is obtained by gel permeation chromatography.

Gaseous components in EX 7.1 to 7.8 were determined to contain >95% of $CO_2$ with minor amount of hydrocarbons, and CO. Only minor changes in composition of gas were noted between different reaction conditions.

TABLE 11

Process conditions and process yields.

| Process conditions | | | | Process yields | | | |
|---|---|---|---|---|---|---|---|
| Temp. °C. | Pressure bar | Inert gas ratio liter/liter | Residence time $h^{-1}$ | Gas yield % | Oil yield <115° C. % | Oil yield >115° C. % | Experiment |
| 300 | 21 | — | 1.3 | 0 | 2 | 98 | EX 7.1 |
| 323 | 23 | — | 1.3 | 7 | 11 | 82 | EX 7.2 |
| 339 | 23 | — | 1.3 | 15 | 19 | 66 | EX 7.3 |
| 316 | 23 | — | 1.4 | 6 | 6 | 88 | EX 7.4 |
| 325 | 23 | — | 2.1 | 4 | 7 | 89 | EX 7.5 |
| 335 | 22 | — | 2.1 | 12 | 12 | 76 | EX 7.6 |
| 300 | 22 | — | 0.7 | 5 | 4 | 91 | EX 7.7 |
| 316 | 23 | — | 1.4 | 13 | 16 | 71 | EX 7.8 |

TABLE 12

Oil >115° C. product distributions.

Oil composition of >115° C. fraction

| Mono-mer area-% | Dimer area-% | Trimer area-% | Tetra-mer area-% | Penta-mer area-% | Hexamer or heavier area-% | Experiment |
|---|---|---|---|---|---|---|
| 80 | 15 | 3 | 1 | 1 | 0 | EX 7.1 |
| 44 | 19 | 13 | 9 | 8 | 7 | EX 7.2 |
| 27 | 17 | 15 | 10 | 13 | 18 | EX 7.3 |
| 57 | 18 | 11 | 6 | 5 | 2 | EX 7.4 |
| 59 | 19 | 11 | 6 | 4 | 1 | EX 7.5 |
| 41 | 20 | 14 | 9 | 10 | 7 | EX 7.6 |
| 65 | 15 | 8 | 5 | 4 | 2 | EX 7.7 |
| 28 | 18 | 15 | 12 | 14 | 13 | EX 7.8 |

Example 8

Levulinic acid was subjected to thermal treatment at a temperature of 300° C. and a pressure of 20 bar with a weight hourly space velocity (WHSV) of 0.7 $h^{-1}$, a gas/hydrocarbons (He as carrier gas) of 800 Nl/l.

The oligomerization product above was subjected to hydrodeoxygenation reactions to remove heteroatoms and to stabilize the oil product.

The hydrodeoxygenation reactions were conducted in presence sulphided NiMo on alumina carrier catalyst at a temperature of 306° C. and under a pressure of 80 bar, using hydrogen to hydrocarbon ($H_2$/HC) ratio of 2184 Nl/l and weight hourly space velocity (WHSV) of 0.3 $h^{-1}$.

The product distribution for the hydrodeoxygenated product obtained with the thermal treatment is presented in table 13 below:

TABLE 13

Oil product distribution.

| | |
|---|---|
| $H_2O$ | 31.3% |
| $CO_2$ | 18.2% |
| C1-C4 | 3.8% |
| C5-C9 | 11.5% |
| TA-180° C. | 7.0% |
| 180-370° C. | 14.4% |
| >370° C. | 13.7% |
| Total | 100% |

The C1-C4 and C5-C9 fractions are gas phase fractions and is a result of some part of the heavier components being shifted to gas phase during the HDO step. They were therefore not part of the distilled gasoline fraction but separated during the HDO run from liquid phase.

The "TA-180° C." fraction was used as the gasoline fraction and analysed using a PIONA analyser (Paraffins, Iso-paraffins, Olefins, Naphthenes, Aromatics and Oxygenates). The results are given in table 14 below, where sample compounds are identified via GC-MS (gas chromatography-mass spectrometry). The content of benzene and toluene are determined via the standard method EN12177, oxygenates with the standard method EN 13132, and relative contents of hydrocarbons with GC-FID (gas chromatography-flame ionization detector). The relative weight response factors in GC-FID analysis for all hydrocarbons (except benzene and toluene) are assumed to be 1.

The absolute contents of hydrocarbons are generated by normalizing the sum of relative content of hydrocarbons acquired via GC-FID, the absolute contents of toluene, benzene and oxygenates to 100 wt-%. Finally, the contents of various analytes are divided according to chemical identity in to representing compound groups.

TABLE 14

PIONA analysis

| Name | Calc p-% | Carbon number |
|---|---|---|
| 1-methyl-2-propyl-cyclopentane | 17.3 | 9 |
| $C_{10}H_{20}$-Cyclo(hexanes/pentanes) | 12.06 | 10 |
| 1-ethyl-4-methyl-cyclohexane | 4.5 | 9 |
| 4-Methyl-octane | 4.51 | 9 |
| $C_9$-Dicyclonapthens | 3.90 | 9 |
| $C_8H_{16}$-Naphtens | 3.50 | 8 |
| 3-Pentanol | 3.24 | 5 |
| 3-Methyl-octane | 2.65 | 9 |
| n-Nonane | 2.64 | 9 |
| 4-Methyl-nonane | 2.49 | 10 |
| 3,4-Dimethyl-hexane | 2.48 | 8 |
| $C_{10}H_{18}$-Cyclo-olefins | 2.42 | 10 |
| $C_9H_{18}$-Naphtens | 2.28 | 9 |
| $C_3$-Cyclohexanes | 2.22 | 9 |
| $C_{11}H_{20}$-Naphtens | 2.01 | 11 |
| 1,2,3-trimethylcyclohexane | 2.00 | 9 |
| 3,4-dimethyl-heptane | 1.70 | 9 |
| Methyl-propyl-cyclopentane | 1.50 | 9 |
| n-Octane | 1.49 | 8 |
| Methyl-cyclohexane | 1.14 | 7 |
| 1-cis-3-dimethyl-cyclohexane | 1.05 | 8 |
| $C_{10}$-Paraffins | 1.03 | 10 |
| $C_{11}H_{22}$-Naphtens | 1.00 | 11 |
| 3-Methyl-heptane | 0.87 | 8 |
| n-Pentane | 0.81 | 5 |
| cis-1-methyl-3-ethyl-cyclopentane | 0.71 | 8 |

TABLE 14-continued

| PIONA analysis | | |
|---|---|---|
| Name | Calc p-% | Carbon number |
| 3-ethyl-4-methyl-hexane | 0.70 | 9 |
| Methyl-cyclopentane | 0.41 | 6 |
| Other | 17.39 | |

It will therefore be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A method for increasing the molecular weight of ketoacids, the method comprising:
    a) providing in a reactor a feedstock containing at least 80 wt % of at least one ketoacid; and
    b) subjecting the feedstock to one or more C-C-coupling reaction(s) to produce a C-C-coupling reaction product; wherein the one or more C-C-coupling reaction(s) are conducted by heating the feedstock to a temperature of 205-400° C. in an absence of a catalyst, and wherein the one or more C-C-coupling reaction(s) are conducted mainly in the liquid phase.

2. The method according to claim 1, wherein the feedstock is heated to a temperature of 245-350° C.

3. The method according to claim 1, wherein the one or more C-C-coupling reaction(s) are conducted in a single reactor.

4. The method according to claim 1, wherein the one or more C-C-coupling reaction(s) are conducted at a pressure of between 10-100 bar.

5. The method according to claim 1, wherein the feedstock contains at least 90 wt-% of at least one ketoacid.

6. The method according to claim 1, wherein the feedstock further comprises an ester of a ketoacid.

7. The method according to claim 1, wherein the feedstock comprises levulinic acid.

8. The method according to claim 1, further comprising subjecting the C-C-coupling reaction product to a hydrodeoxygenation step and optionally an isomerization step to produce a hydrocarbon product.

9. The method according to claim 8, wherein the hydrodeoxygenation step is conducted in the presence of a hydrodeoxygenation catalyst comprising a hydrogenation metal on a support.

10. The method according to claim 8, wherein the method comprises subjecting the C-C-coupling reaction product to a hydrodeoxygenation step and an isomerization step, and wherein said isomerization step is conducted in the presence of an isomerization catalyst.

11. The method according to claim 1, wherein the C-C-coupling reaction(s) are conducted at a pressure of between 10-50 bar.

12. The method according to claim 2, wherein the C-C-coupling reaction(s) are conducted at a pressure of between 10-100 bar.

* * * * *